(12) United States Patent
Zhang

(10) Patent No.: US 11,690,724 B2
(45) Date of Patent: Jul. 4, 2023

(54) METAL-CERAMIC COMPOSITE JOINT PROSTHESIS AND APPLICATIONS AND MANUFACTURING METHOD THEREOF

(71) Applicant: Beijing AK Medical Co., Ltd, Beijing (CN)

(72) Inventor: Weiping Zhang, Beijing (CN)

(73) Assignee: BEIJING AK MEDICAL CO., LTD, Beijing (CN)

( * ) Notice: Subject to any disclaimer, the term of this patent is extended or adjusted under 35 U.S.C. 154(b) by 0 days.

(21) Appl. No.: 15/734,679

(22) PCT Filed: Oct. 31, 2019

(86) PCT No.: PCT/CN2019/114541
§ 371 (c)(1),
(2) Date: Dec. 3, 2020

(87) PCT Pub. No.: WO2021/081857
PCT Pub. Date: May 6, 2021

(65) Prior Publication Data
US 2021/0361434 A1 Nov. 25, 2021

(51) Int. Cl.
*A61F 2/30* (2006.01)
*A61F 2/34* (2006.01)
(Continued)

(52) U.S. Cl.
CPC ........ *A61F 2/3094* (2013.01); *A61F 2/30771* (2013.01); *A61F 2/34* (2013.01);
(Continued)

(58) Field of Classification Search
CPC ...... A61F 2/3094; A61F 2/30771; A61F 2/34; A61F 2/3609; A61F 2/3859;
(Continued)

(56) References Cited

U.S. PATENT DOCUMENTS 636,568 A * 11/1899 Seeley .................. A61C 13/30
433/221
3,707,006 A * 12/1972 Bokros ............... A61F 2/30965
433/201.1
(Continued)

FOREIGN PATENT DOCUMENTS

CN   101405039 A   4/2009
CN   201586094 U   9/2010
(Continued)

OTHER PUBLICATIONS

ISR for PCT/CN2019/114541, Jul. 30, 2020.
European Search Report, dated May 24, 2021.

*Primary Examiner* — Brian A Dukert
*Assistant Examiner* — Melissa A Hoban
(74) *Attorney, Agent, or Firm* — AKC Patents, LLC; Aliki K. Collins

(57) ABSTRACT

The present invention discloses a metal-ceramic composite joint prosthesis and applications and a manufacturing method thereof. The joint prosthesis comprises a metal body and a ceramic body, wherein the metal body is integrally formed and comprises a porous structure layer, a boundary layer and a root-like layer, the boundary layer is located between the porous structure layer and the root-like layer, the root-like layer comprises a plurality of root-like filament clusters connected to the boundary layer but not in contact with one another, each root-like filament cluster comprises a main root perpendicularly connected to the boundary layer and a plurality of fibrous roots connected to the lateral side of the main root, the fibrous roots extend obliquely towards the side away from the boundary layer, and the ceramic body covers the root-like filament clusters and is formed on the boundary layer. The joint prosthesis achieves the compositing of metal and ceramic, thereby achieving both a wear-resistant ceramic body required for a joint friction surface (Continued)

and a porous metal structure with a good bone ingrowth effect required for an osseointegration surface. The root-like filament clusters of the root-like layer are rooted in the ceramic body, to form a tight and stable connection between the ceramic body and the metal body, and the root-like clusters being not in contact with one another prevents the ceramic body from locally breaking or cracking.

17 Claims, 8 Drawing Sheets

(51) Int. Cl.
  *A61F 2/36* (2006.01)
  *A61F 2/38* (2006.01)
  *B33Y 10/00* (2015.01)

(52) U.S. Cl.
  CPC .......... *A61F 2/3609* (2013.01); *A61F 2/3859* (2013.01); *B33Y 10/00* (2014.12); *A61F 2002/30156* (2013.01); *A61F 2002/30242* (2013.01); *A61F 2002/30784* (2013.01); *A61F 2002/30943* (2013.01); *A61F 2002/30968* (2013.01); *A61F 2002/30973* (2013.01); *A61F 2002/30985* (2013.01); *A61F 2002/3611* (2013.01); *A61F 2310/00011* (2013.01); *A61F 2310/00179* (2013.01)

(58) Field of Classification Search
  CPC .. A61F 2002/30156; A61F 2002/30242; A61F 2002/30784; A61F 2002/30943; A61F 2002/30968; A61F 2002/30973; A61F 2002/30985; A61F 2002/3611; A61F 2310/00011; A61F 2310/00179; A61F 2/30767; A61F 2/36; A61F 2/3601; A61F 2/389; A61F 2002/30004; A61F 2002/30011; A61F 2002/30024; A61F 2002/30316; A61F 2002/30329; A61F 2002/30331; A61F 2002/30332; A61F 2002/30838; A61F 2002/3092; A61F 2002/30957; A61F 2002/30971; A61F 2002/3445; A61F 2002/3446; A61F 2310/00035; A61F 2310/00173; A61F 2/30965; A61F 2/32; A61F 2/38; B33Y 10/00

See application file for complete search history.

(56) References Cited

U.S. PATENT DOCUMENTS

| | | | | |
|---|---|---|---|---|
| 3,855,638 A * | 12/1974 | Pilliar | .............. | A61F 2/30 433/173 |
| 4,145,764 A * | 3/1979 | Suzuki | .............. | A61F 2/30767 606/76 |
| 4,355,429 A | 10/1982 | Mittelmeier et al. | | |
| 4,542,539 A * | 9/1985 | Rowe, Jr. | .............. | A61F 2/30 606/76 |
| 4,553,272 A * | 11/1985 | Mears | .............. | A61L 27/56 623/10 |
| 4,713,076 A * | 12/1987 | Draenert | .............. | A61L 27/32 606/77 |
| 4,863,475 A * | 9/1989 | Andersen | .............. | A61L 27/56 623/901 |
| 4,904,264 A * | 2/1990 | Scheunemann | ..... | A61F 2/30907 623/23.57 |
| 5,167,271 A * | 12/1992 | Lange | .............. | B22D 19/14 264/610 |
| 5,306,311 A * | 4/1994 | Stone | .............. | C08L 1/00 623/14.12 |
| 5,716,414 A | 2/1998 | Caldarise | | |
| 5,915,970 A * | 6/1999 | Sicurelli, Jr. | .......... | A61C 13/30 433/220 |
| 6,147,135 A * | 11/2000 | Yuan | .............. | A61F 2/30965 604/93.01 |
| 8,043,382 B2 * | 10/2011 | Kumar | .............. | A61F 2/34 623/23.54 |
| 10,639,160 B2 * | 5/2020 | Hanson | .............. | A61F 2/36 |
| 2003/0171820 A1 * | 9/2003 | Wilshaw | .............. | C23C 28/321 623/23.57 |
| 2005/0049713 A1 * | 3/2005 | Garber | .............. | A61F 2/34 623/22.21 |
| 2006/0105015 A1 * | 5/2006 | Perla | .............. | A61L 31/022 424/602 |
| 2006/0235542 A1 * | 10/2006 | Hodorek | .............. | A61F 2/30756 623/23.51 |
| 2007/0116734 A1 * | 5/2007 | Akash | .............. | A61F 2/30 264/44 |
| 2007/0142914 A1 * | 6/2007 | Jones | .............. | B23K 26/382 623/14.13 |
| 2007/0208428 A1 * | 9/2007 | Tepic | .............. | A61F 2/3603 623/22.32 |
| 2007/0244484 A1 * | 10/2007 | Luginbuehl | ......... | A61L 27/3654 606/86 R |
| 2010/0009103 A1 * | 1/2010 | Kuboki | .............. | A61F 2/32 428/319.1 |
| 2010/0174377 A1 * | 7/2010 | Heuer | .............. | A61L 27/30 435/395 |
| 2010/0268337 A1 * | 10/2010 | Gordon | .............. | A61F 2/28 428/218 |
| 2011/0125277 A1 * | 5/2011 | Nygren | .............. | A61F 2/30 623/20.14 |
| 2012/0153548 A1 * | 6/2012 | Landingham | ......... | F41H 5/0414 264/643 |
| 2013/0006354 A1 * | 1/2013 | Pressacco | .............. | A61F 2/30 623/11.11 |
| 2013/0281793 A1 * | 10/2013 | Chen | .............. | A61N 1/3925 600/300 |
| 2018/0014937 A1 * | 1/2018 | Fonte | .............. | A61F 2/30767 |
| 2018/0021138 A1 * | 1/2018 | Estes | .............. | A61F 2/30756 623/16.11 |

FOREIGN PATENT DOCUMENTS

| | | |
|---|---|---|
| CN | 204671321 U | 9/2015 |
| CN | 205163319 U | 4/2016 |
| CN | 105796211 A | 7/2016 |
| EP | 672395 A1 | 9/1995 |
| WO | 2008061216 A2 | 5/2008 |

* cited by examiner

METAL-CERAMIC COMPOSITE JOINT PROSTHESIS AND APPLICATIONS AND MANUFACTURING METHOD THEREOF

FIELD

The present invention relates to the field of orthopedic implants, in particular to a metal-ceramic composite joint prosthesis and applications and a manufacturing method thereof.

BACKGROUND

At present, implant products in artificial joint replacement surgery usually have two very important surfaces, namely, a joint friction surface and an osseointegration interface. Due to the contact friction between each joint friction surface and a contralateral joint friction surface forming a joint friction pair, they need to have good friction performance, comprising sufficient hardness and toughness, a low wear rate, good lubricating properties, and anti-deformation strength, to meet functional requirements. Nowadays, it is generally recognized in the industry that a ceramic interface serving as a joint friction surface on one or even two sides of a friction pair can effectively reduce wear of an articular surface. An osseointegration interface is an interface for contact between an implant and a human bone. Researches in recent years show that a surface of a porous metal has a good bone ingrowth effect, and permits human bone cell tissue to easily grow into pores inside the porous material, thereby achieving effective fusion between the bone tissue and the porous metal, so that the implant can be firmly fixed to the human bone.

It is difficult to make a ceramic material into a porous structure and the ceramic material cannot achieve ingrowth of bone cells, while a joint friction surface made of a metal material cannot achieve excellent wear resistance of the ceramic material.

SUMMARY

In view of the problems existing in the prior art, an object of the present invention is to provide a metal-ceramic composite joint prosthesis and applications and a manufacturing method thereof. In the joint prosthesis, a joint friction surface made of a ceramic and an osseointegration interface made of a porous metal are integrated into one joint prosthesis, thereby not only reducing the wear of the joint friction surface, but also ensuring a good bone ingrowth effect.

To achieve the above object, a technical solution of the present invention is as follows:

A metal-ceramic composite joint prosthesis comprises a metal body and a ceramic body, wherein the metal body is integrally formed and comprises a porous structure layer, a boundary layer and a root-like layer, the boundary layer is located between the porous structure layer and the root-like layer, the root-like layer comprises a plurality of root-like filament clusters connected to the boundary layer but not in contact with one another, each root-like filament cluster comprises a main root perpendicularly connected to the boundary layer and a plurality of fibrous roots connected to the lateral side of the main root, the fibrous roots extend obliquely towards the side away from the boundary layer, and the ceramic body covers the root-like filament clusters and is formed on the boundary layer.

Further, the part of each fibrous root connected with the main root is close to the joint between the main root and the boundary layer.

Further, the boundary layer is a plate-like structure, and a plurality of root-like filament clusters are regularly connected to the surface of the boundary layer.

Further, a plurality of regularly arranged grooves are disposed on the plate-like structure, and support walls are formed between adjacent grooves, and the root-like filament clusters are connected to upper surfaces of intersections of different support walls.

Further, the grooves are of cubic structures, and each root-like filament cluster is connected to the upper surface of the intersection of four mutually perpendicular support walls.

Further, the support walls have a thickness of 0.1-3 mm and a height of 0.25-2.5 mm.

Further, a plurality of regularly arranged bar-like reinforcing ribs are disposed on the plate-like structure, and the root-like filament clusters are connected at equal intervals to upper surfaces of the reinforcing ribs.

Further, the boundary layer is provided with the reinforcing ribs in two directions perpendicular to one another, with a plurality of reinforcing ribs being disposed in each direction.

Further, the reinforcing ribs have a thickness of 0.1-3 mm and a height of 0.25-2.5 mm.

Further, the material of the metal body is a tantalum metal or tantalum alloy.

Further, the pore diameter of the porous structure layer is 50-1200 μm.

Further, the material of the ceramic body is an alumina-based ceramic, a zirconia-based ceramic, or a silicon carbide-based ceramic.

Further, an included angle between axes of each fibrous root and the main root is less than or equal to 45°.

Further, the included angle between the axes of each fibrous root and the main root is 30°.

Further, the diameters of the main root and the fibrous roots are both 0.1-2 mm.

Further, connecting lines of centers of projections of every three of the root-like filament clusters adjacent and closest to one another on the boundary layer form an equilateral triangle.

The present invention also provides an application of the above-mentioned joint prosthesis, a technical solution of which is as follows:

A hip joint prosthesis comprises: a hip ball prosthesis mounted on a human femur, and a hip acetabular cup prosthesis matched with the hip ball prosthesis, the hip ball prosthesis and the hip acetabular cup prosthesis being both made of the above-mentioned joint prosthesis, wherein the boundary layer of the hip ball prosthesis is a curved plate-like structure, and the boundary layer of the hip ball prosthesis is a structure formed after a flat plate is bent multiple times.

The present invention also provides another application of the above-mentioned joint prosthesis, a technical solution of which is as follows:

A knee joint prosthesis comprises a knee femoral condyle prosthesis mounted to a tibial plateau, the knee femoral condyle prosthesis being made of the above-mentioned joint prosthesis, wherein the boundary layer of the knee femoral condyle prosthesis is a structure formed after a flat plate is bent multiple times.

The present invention also provides a manufacturing method of the above-mentioned metal-ceramic composite joint prosthesis, comprising:

designing a three-dimensional model of the metal body;

inputting a file of the three-dimensional model into a 3D printing device for 3D printing;

implanting the printed metal body into a forming mold of the ceramic body, filling one side of the root-like layer with ceramic blank powder and a sintering aid adhesive, and closing the forming mold for pressing the ceramic blank powder and the sintering aid adhesive to form a pre-sintering blank;

placing the pre-sintering blank after shaping into a sintering furnace for sintering to form a ceramic body bonded to the root-like filament clusters; and polishing a joint friction surface on the ceramic body.

Figure 1:
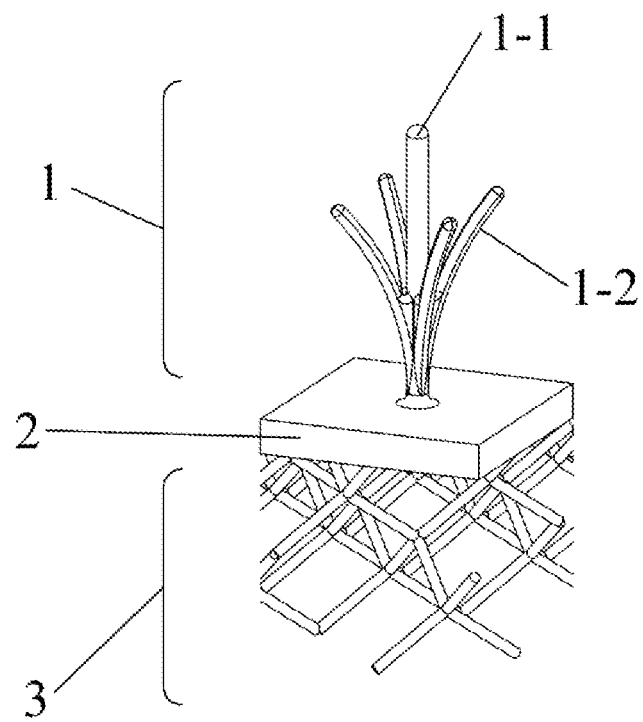
FIG. 1 is a structural schematic diagram of a single root-like filament cluster connected to a metal body in embodiment 1 of the present invention.

REFERENCE NUMERALS 1. root-like layer; 1-1. main root; 1-2. fibrous root;
2. boundary layer; 2-1. groove; 2-2. support wall; 2-3. reinforcing rib;
3. porous structure layer; 4. ceramic body; 5. forming mold; 6. hip ball prosthesis; 7. hip acetabular cup prosthesis; 8. human femur; 9. knee femoral condyle prosthesis; 10. knee joint spacer; 11. knee tibial plateau prosthesis.

DETAILED DESCRIPTION OF THE EMBODIMENTS

To clearly describe the design idea of the present invention, the present invention will be described in conjunction with examples.

To enable those skilled in the art to better understand the solutions of the present invention, the technical solutions in examples of the present invention will be described below clearly and completely in conjunction with the accompanying drawings in the examples of the present invention. Obviously, the described examples are only a part of the examples of the present invention, and not all the examples. All other embodiments obtained by those of ordinary skill in the art without creative work, based on the examples in the present invention, fall into the protection scope of the present invention.

In description of the embodiments, orientation or location relations denoted by the terms "upper", "lower", and the like are orientation or location relations based on illustration in the drawings, are only intended to facilitate describing the present invention and simplify description, instead of indicating or implying the denoted devices or elements necessarily have specific orientations and are constructed and operated in specific orientations, and thus they cannot be understood as limiting the present invention.

It needs to be noted that terms as used herein are only for describing specific embodiments, and are not intended to limit exemplary embodiments according to the present application. As used herein, unless the context clearly indicates otherwise, a singular form is also intended to include a plural form. In addition, it should also be understood that the terms "include" and/or "comprise" when used in this specification, indicate the presence of features, steps, operations, devices, components, and/or combinations thereof.

Embodiment 1

The embodiment shown in FIGS. 1-7 provides a metal-ceramic composite prosthesis of the present invention, comprising a metal body and a ceramic body 4, wherein the metal body is integrally formed and comprises a porous structure layer 3, a boundary layer 2 and a root-like layer 1, the boundary layer 2 is located between the porous structure layer 3 and the root-like layer 1, the root-like layer 1 comprises a plurality of root-like filament clusters connected to the boundary layer but not in contact with one another, each root-like filament cluster comprises a main root 1-1 perpendicularly connected to the boundary layer and a plurality of fibrous roots 1-2 connected to the lateral side of the main root, the fibrous roots 1-2 extend obliquely towards the side away from the boundary layer; and the ceramic body 4 covers the root-like filament clusters and is formed on the boundary layer 2.

The metal-ceramic composite joint prosthesis of this embodiment achieves the compositing of metal and ceramic in one joint prosthesis product, thereby achieving both a wear-resistant ceramic body 4 required for a joint friction surface and a porous metal structure 3 with a good bone ingrowth effect required for an osseointegration surface. The root-like filament clusters of the root-like layer 1 are rooted in the ceramic body 4, to form a tight and stable connection between the ceramic body 4 and the metal body, and the root-like clusters being not in contact with one another avoids internal stress concentration of the ceramic body 4 caused by local isolation of the ceramic body 4 due to contact between the root-like filament clusters in a cooling process of the joint prosthesis product after sintering of the ceramic body 4, to prevent the ceramic body 4 from locally breaking or cracking.

The metal body in this embodiment can be obtained by 3D printing, metal particle sintering, high temperature spraying or the like, and the material of the metal body is a tantalum metal or tantalum alloy, which is selected specifically according to the use requirement of and the application cost of the joint; and the pore diameter of the porous structure layer 3 is 50-1200 μm. The material of the ceramic body in this embodiment can be an alumina-based ceramic, a zirconia-based ceramic, a silicon carbide-based ceramic, or other ceramic material that meets medical implantation requirements.

Figure 6:
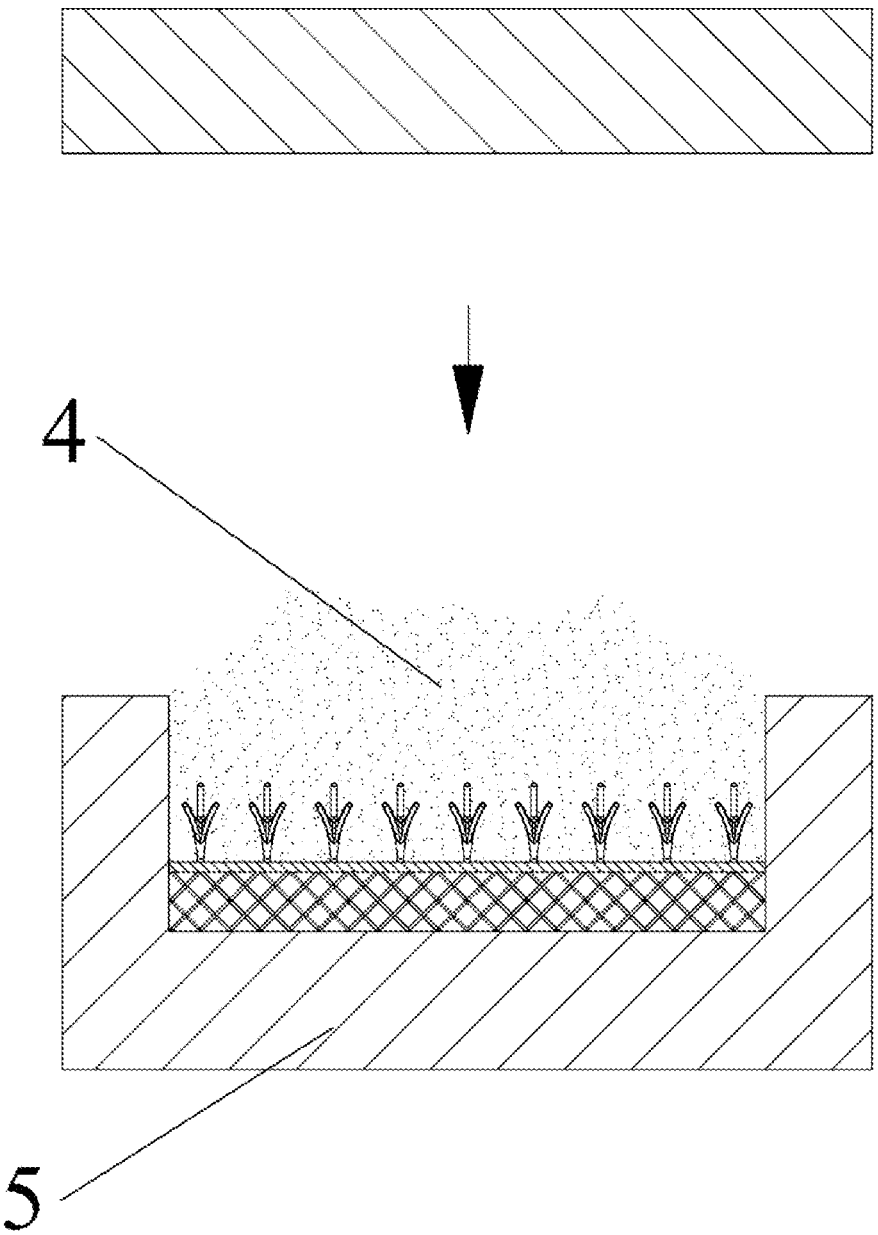
FIG. 6 is a forming process schematic diagram of embodiment 1 of the present invention.
Figure 7:
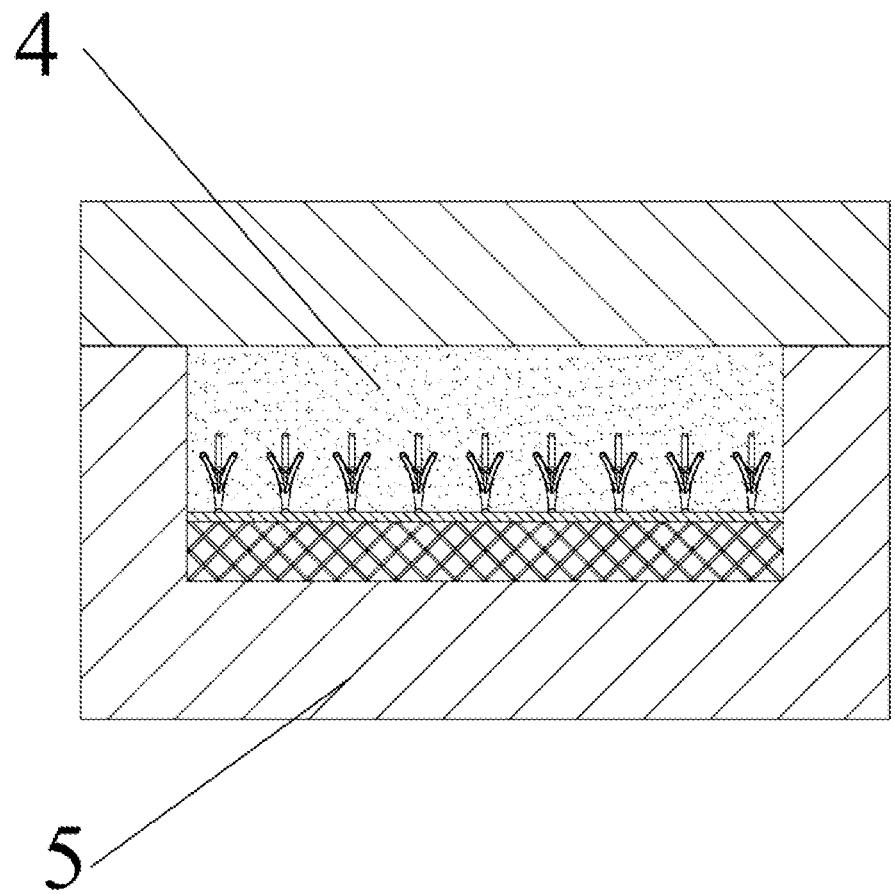
FIG. 7 is a forming schematic diagram of embodiment 1 of the present invention.

As shown in FIGS. 6 and 7, the ceramic body 4 is formed on the boundary layer by sintering ceramic blank powder covering the root-like filament clusters. During sintering of the ceramic body 4, the root-like filament clusters and the ceramic body 4 deform to different degrees due to different thermal expansion coefficients. When the root-like filament clusters and the ceramic body 4 generate internal stress, due to good ductility of the tantalum metal or tantalum alloy itself, the root-like filament clusters can deform by itself to adapt to the deformation of the ceramic body 4, thereby reducing the internal stress, so that the root-like filament clusters and the ceramic body 4 can be bonded more tightly. In this embodiment, the material of the ceramic body 4 is selected from the alumina-based ceramic, zirconia-based ceramic or silicon carbide-based ceramic because thermal expansion coefficients of the above-mentioned materials are very approximate to that of tantalum, wherein the thermal expansion coefficient of the alumina ceramic is $7.5 \times 10^{-6}/^\circ$ C., the thermal expansion coefficient of the zirconia is $9.6 \times 10^{-6}/^\circ$ C., the thermal expansion coefficient of the silicon carbide is $4.7 \times 10^{-6}/^\circ$ C., and the thermal expansion coefficient of the tantalum metal is $6.6 \times 10^{-6}/^\circ$ C., such that the ceramic body 4 and the root-like filament clusters have similar thermal expansion. In addition, the melting point of the tantalum metal is as high as 2995° C., which is much higher than the sintering temperature of the ceramic, so that the ceramic body 4 and the root-like filament clusters will not generate unnecessary internal stress due to an excessive difference in thermal expansion coefficient, thereby further ensuring that the root-like filament clusters and the ceramic body 4 can be bonded more tightly.

Figure 2:
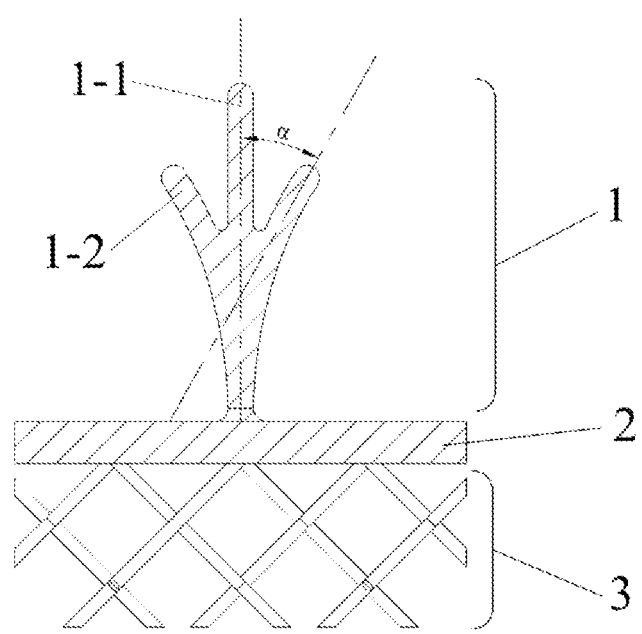
FIG. 2 is a sectional structural schematic diagram of FIG. 1.

As shown in FIG. 1, the part of each fibrous root 1-2 connected with the main root 1-1 is close to the joint between the main root 1-1 and the boundary layer 2, so that the fibrous root 1-2 can be more firmly connected to the main root 1-1. As shown in FIG. 2, an included angle α between axes of each fibrous root 1-2 and the main root 1-1 is less than or equal to 45°, and in this embodiment, α=30°, so as not to generate excessive tensile stress or compressive stress on the ceramic body between the fibrous roots 1-2 and the boundary layer 2 during the sintering of the ceramic body 4.

Figure 5:
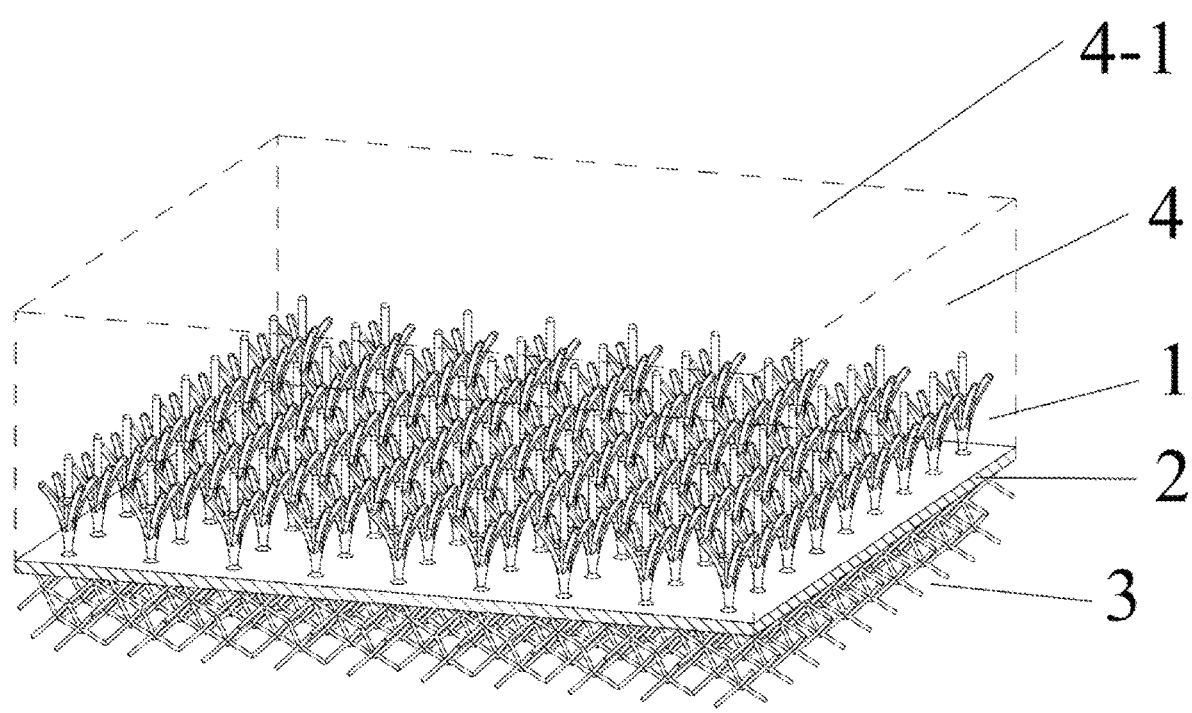
FIG. 5 is a structural schematic diagram of embodiment 1 of the present invention.

As shown in FIG. 5, the boundary layer 2 in this embodiment is a plate-like structure, and a plurality of root-like filament clusters are regularly connected to the surface of the boundary layer 2.

Figure 3:
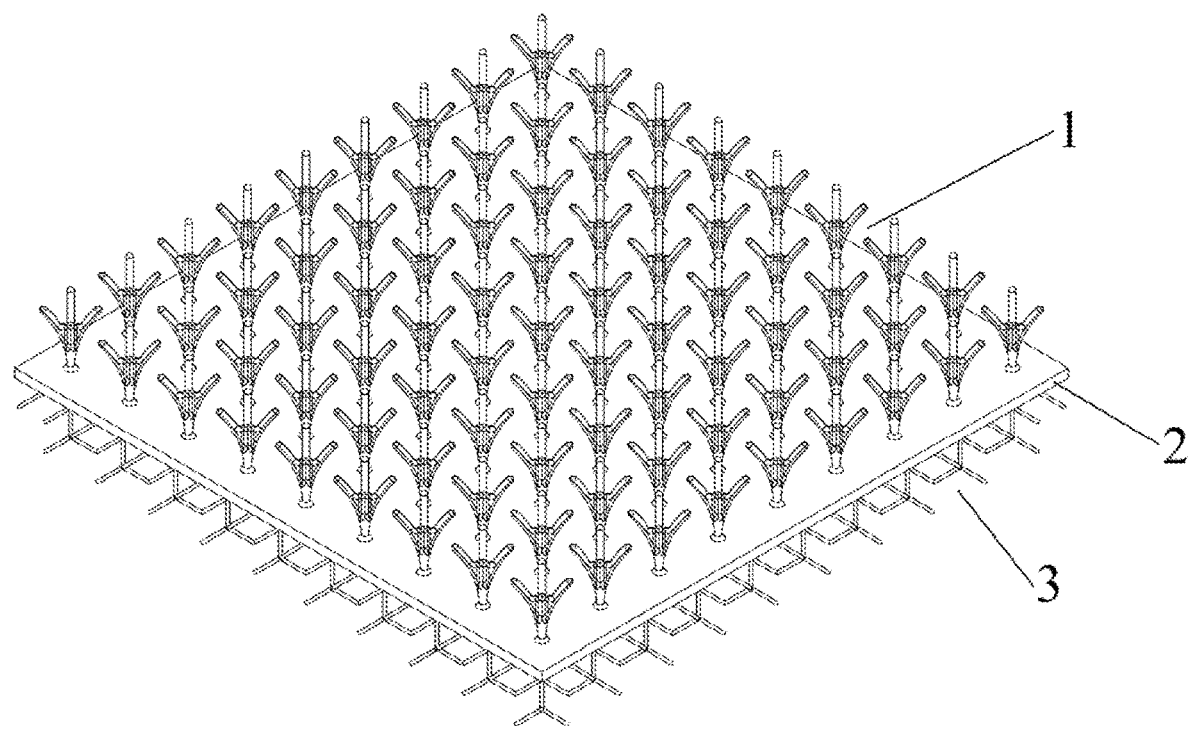
FIG. 3 is a structural schematic diagram of the metal body in embodiment 1 of the present invention.
Figure 4:
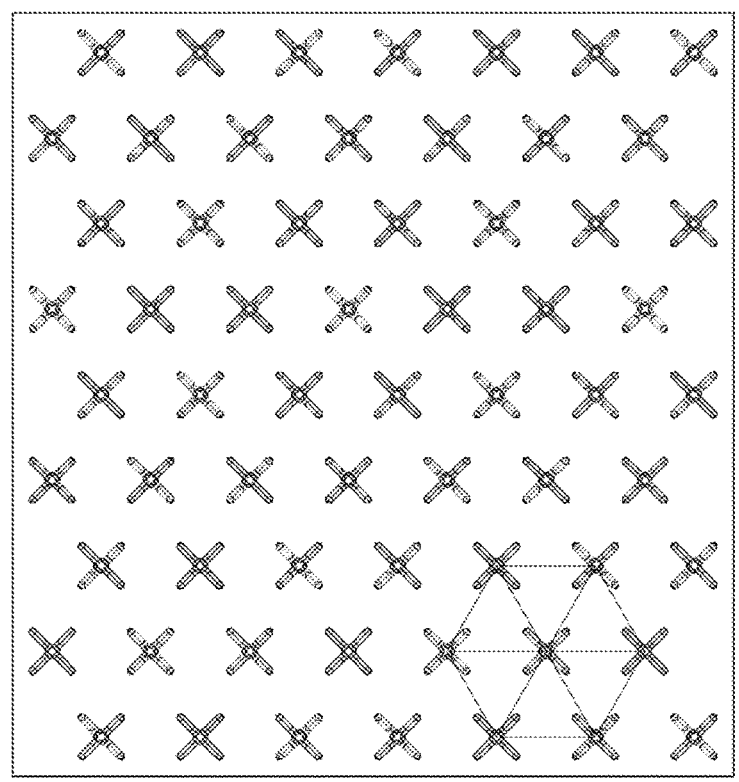
FIG. 4 is a top-view schematic diagram of FIG. 3.

Connecting lines of centers of projections of every three of the root-like filament clusters adjacent and closest to one another on the boundary layer form an equilateral triangle. As shown in FIGS. 3 and 4, vertical distances between adjacent horizontal rows of root-like filament clusters are equal, root-like filament clusters in different horizontal rows are arranged at intervals, and distances between adjacent root-like filament clusters are equal. In this arrangement of the root-like filament clusters, the root-like filament clusters are evenly distributed in the ceramic body 4, and adjacent root-like filament clusters in all directions of the ceramic body 4 are equally spaced, so that the root-like filament clusters can bear the load more uniformly.

The diameters of the main root 1-1 and the fibrous roots 1-2 are both 0.1-2 mm.

Figure 8:
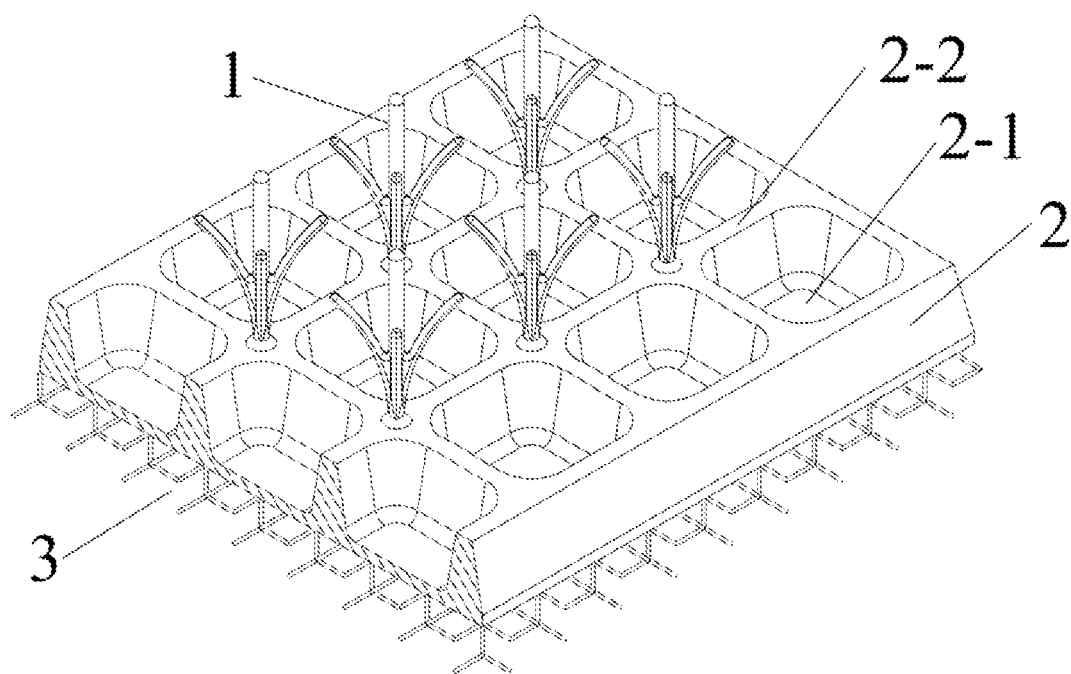
FIG. 8 is a structural schematic diagram of a second type of boundary layer in embodiment 1 of the present invention.

The boundary layer 2 in this embodiment can be a flat plate-like structure as shown in FIG. 5, or can also be a structure as shown in FIG. 8, that is, a plurality of regularly arranged grooves 2-1 are disposed on the plate-like structure shown in FIG. 5, and support walls 2-2 are formed between adjacent grooves, and the root-like filament clusters are connected to upper surfaces of intersections of different support walls 2-2. As shown in FIG. 8, the grooves 2-1 are of cubic structures. When the grooves are formed, it needs to ensure that the thickness of the bottom wall of each groove meets the strength requirement. Each root-like filament cluster is connected to the upper surface of the intersection of four mutually perpendicular support walls 2-2. The arrangement of the support walls 2-2 can increase the strength of the boundary layer 2, and connecting the root-like filament clusters to the upper surfaces of the intersections of different support walls 2-2 ensures the connection strength between the root-like filament clusters and the boundary layer 2. The support walls 2-2 have a thickness of 0.1-3 mm and a height of 0.25-2.5 mm.

Figure 9:
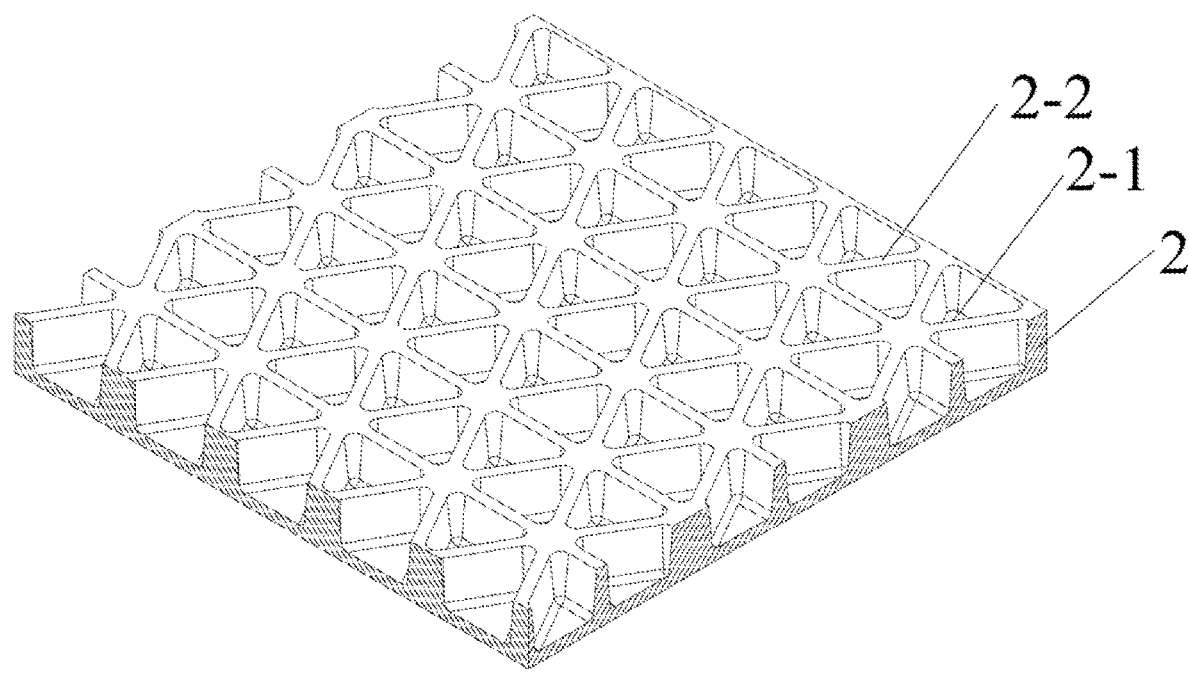
FIG. 9 is a structural schematic diagram of a third type of boundary layer in embodiment 1 of the present invention.

In this embodiment, the spatial form of the grooves 2-1 is not limited to a cubic structure, but can also be in other shapes, such as cylindrical, prismatic and other irregular three-dimensional shapes. The grooves 2-1 of the boundary layer in FIG. 9 are in a tri-prismatic shape.

Figure 10:
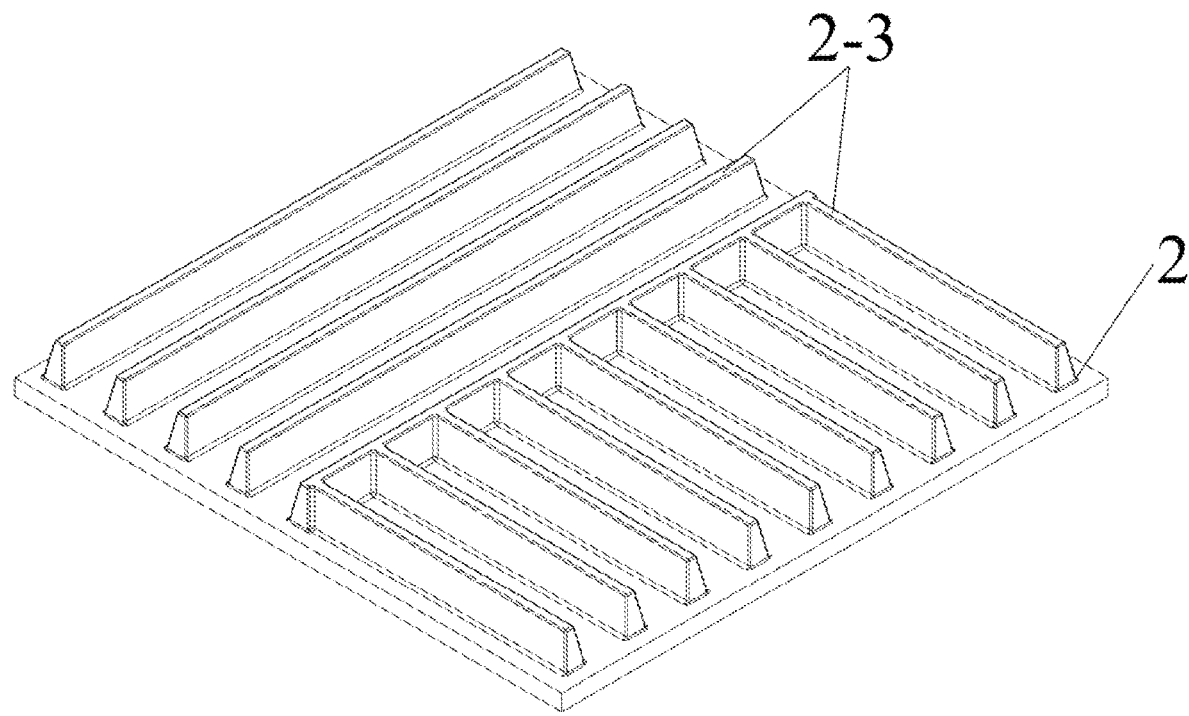
FIG. 10 is a structural schematic diagram of a fourth type of boundary layer in embodiment 1 of the present invention.

In this embodiment, the boundary layer 2 can also be a structure as shown in FIG. 10, in which a plurality of regularly arranged bar-like reinforcing ribs 2-3 are disposed on the plate-like structure, and the root-like filament clusters are connected at equal intervals to upper surfaces of the reinforcing ribs 2-3. As shown in FIG. 10, the boundary layer is provided with reinforcing ribs 2-3 in two directions perpendicular to one another, with a plurality of reinforcing ribs being disposed in each direction, and the root-like filament clusters are connected at equal intervals to the upper surface of the reinforcing ribs 2-3, and the reinforcing ribs 2-3 have a thickness of 0.1-3 mm and a height of 0.25-2.5 mm.

The boundary layer of the present invention can also be configured as a structure of a combination of at least two of a flat plate, grooves and reinforcing ribs according to the shape of a patient's bone bed and biomechanical considerations.

Figure 11:
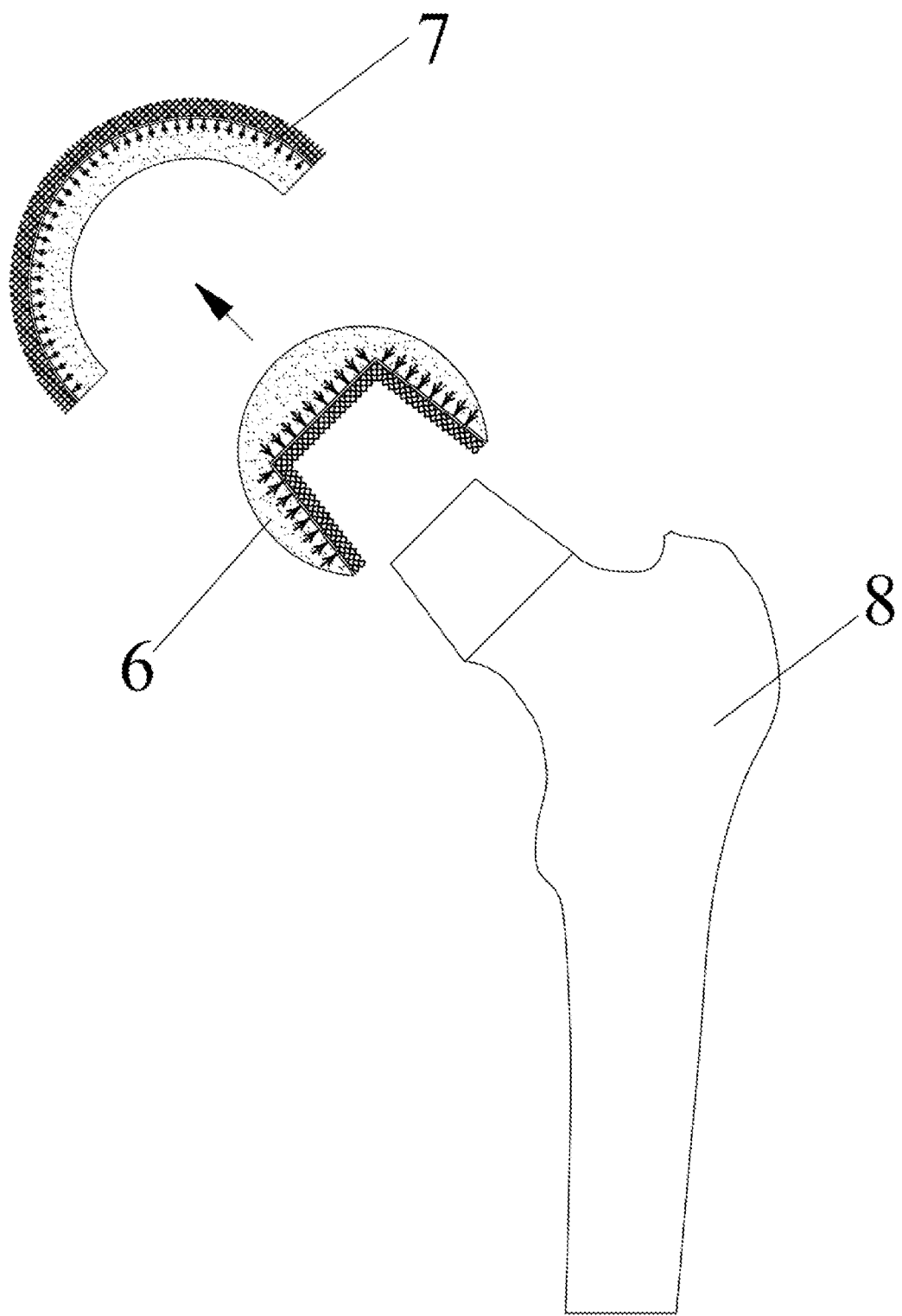
FIG. 11 is a schematic diagram of a first application example of the present invention.
Figure 12:
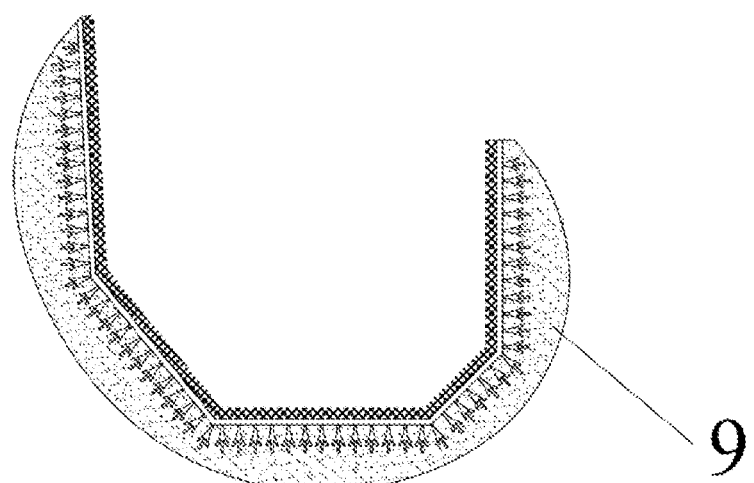
FIG. 12 is a schematic diagram of a second application example of the present invention.
Figure 12:
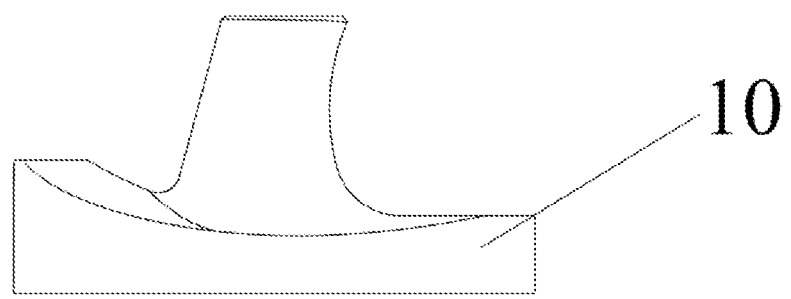
Figure 12:
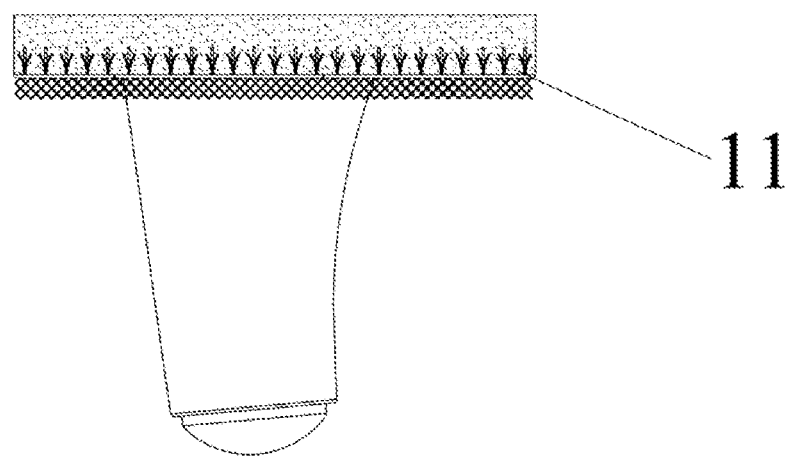

In the joint prosthesis in this embodiment, the porous structure layer is connected with a human bone to permit the human bone to easily grow into the porous structure layer, so that the joint prosthesis can be biologically fixed to achieve the purpose of fixing the joint prosthesis more firmly. The metal-ceramic composite joint prosthesis in this embodiment can be applied to various artificial joints, such as a hip joint prosthesis, a knee joint prosthesis, a shoulder joint prosthesis, an ankle joint prosthesis, a temporomandibular joint prosthesis, an elbow joint prosthesis, and a wrist joint prosthesis. As shown in FIGS. 11 and 12, two application examples of the joint prosthesis of the above structure in this embodiment are provided. FIG. 11 shows a schematic diagram of a hip joint prosthesis, and FIG. 12 is a schematic diagram of a knee joint prosthesis. The boundary layer 2 of a knee tibial plateau prosthesis in FIG. 12 is a planar structure, and the rest part of the joint prosthesis is a curved surface structure. In the manufacture of the joint prosthesis, the boundary layer 2 of the metal body can be made into a curved plate-like structure as indicated by a hip acetabular cup prosthesis 7 in FIG. 11, or the boundary layer 2 can also be made into structures formed after a flat plate is bent multiple times as indicated by a hip ball prosthesis 6 in FIG. 11 and a knee femoral condyle prosthesis 9 in FIG. 12. Axes of the root-like filament clusters intersect in both of the two types of structures of the boundary layer 2, and in this case, the root-like filament clusters can be more firmly bonded to the ceramic body 4. Especially when the boundary layer 2 is a curved plate-like structure, the bonding effect of the root-like filament clusters and the ceramic body 4 is better, and relative displacement between the ceramic body 4 and the root-like filament clusters does not occur to cause internal wear of the ceramic body 4. Most joint prostheses have curved surfaces, and require the boundary layer with one of the two types of structures described above, so that the joint prostheses in this embodiment have a longer service life.

Embodiment 2

The present invention also provides a manufacturing method of the metal-ceramic composite joint prosthesis of embodiment 1. The method comprises the following steps:

designing a three-dimensional model of the metal body;

inputting a file of the three-dimensional model into a 3D printing device for 3D printing to obtain the root-like layer 1, the boundary layer 2 and the porous structure layer 3 in embodiment 1, wherein the 3D printing device is a metal 3D printing device;

implanting the printed metal body into a forming mold of the ceramic body, filling one side of the root-like layer with ceramic blank powder and a sintering aid adhesive, and closing the forming mold for pressing the ceramic blank powder and the sintering aid adhesive to form a pre-sintering blank, wherein the existence of the boundary layer 2 blocks the ceramic blank powder from diffusing to the porous structure layer, and provides a forming surface for the pre-sintering blank;

placing the pre-sintered blank after shaping into a sintering furnace for sintering to form a ceramic body 4 bonded to the root-like filament clusters, wherein the purpose of shaping is to provide a good bonding effect of the ceramic blank powder and the root-like filament clusters, so that the shaped ceramic body 4 can be more tightly bonded to the root-like filament clusters; and polishing a joint friction surface on the ceramic body 4 to ensure that the smoothness of the joint friction surface meets the moving friction requirement.

It should be noted that, in addition to the specific embodiments provided above, some of the structures can have different options. These can be made by those skilled in the art based on their basic skills on the basis of understanding the idea of the present invention, and therefore will not be enumerated here.

Finally, it can be understood that the above embodiments are only exemplary embodiments for illustrating the principle of the present invention; however, the present invention is not limited thereto. For those of ordinary skill in the art, various modifications and improvements can be made without departing from the principle and essence of the present invention, and these modifications and improvements are also encompassed within the protection scope of the present invention.

The invention claimed is:

1. A metal-ceramic composite joint prosthesis, comprising a metal body and a ceramic body, wherein the metal body is integrally formed and comprises a porous structure layer, a boundary layer and a root layer, the boundary layer is located between the porous structure layer and the root layer, the root layer comprises a plurality of root filament clusters connected to the boundary layer but not in contact with one another, each root filament cluster comprises a main root perpendicularly connected to the boundary layer and a plurality of fibrous roots connected to a lateral side of the main root, the fibrous roots extend obliquely from the lateral side of the main root away from the boundary layer, the part of each fibrous root connected with the main root extends from a joint between the main root and the boundary layer, and the ceramic body covers the root filament clusters and is formed on the boundary layer; and wherein connecting lines of centers of projections of every three of the root filament clusters adjacent and closest to one another on the boundary layer form an equilateral triangle.

2. The joint prosthesis according to claim 1, wherein the boundary layer has a plate structure, and the plurality of root filament clusters are regularly connected to a surface of the boundary layer.

3. The joint prosthesis according to claim 2, wherein a plurality of regularly arranged grooves are disposed on the plate structure, and support walls are formed between adjacent grooves, and the root filament clusters are connected to upper surfaces of intersections of different support walls.

4. The joint prosthesis according to claim 3, wherein the grooves are of cubic structures, and each root filament cluster is connected to the upper surface of the intersection of four mutually perpendicular support walls.

5. The joint prosthesis according to claim 4, wherein the support walls have a thickness of 0.1-3 mm and a height of 0.25-2.5 mm.

6. The joint prosthesis according to claim 2, wherein a plurality of regularly arranged bar reinforcing ribs are disposed on the plate structure, and the root filament clusters are connected at equal intervals to upper surfaces of the reinforcing ribs.

7. The joint prosthesis according to claim 6, wherein the boundary layer is provided with the reinforcing ribs in two directions perpendicular to one another, with a plurality of reinforcing ribs being disposed in each direction.

8. The joint prosthesis according to claim 7, wherein the reinforcing ribs have a thickness of 0.1-3 mm and a height of 0.25-2.5 mm.

9. The joint prosthesis according to claim 1, wherein a material of the metal body is a tantalum metal or tantalum alloy.

10. The joint prosthesis according to claim 1, wherein a pore diameter of the porous structure layer is 50-1200 µm.

11. The joint prosthesis according to claim 1, wherein a material of the ceramic body is an alumina-based ceramic, a zirconia-based ceramic, or a silicon carbide-based ceramic.

12. The joint prosthesis according to claim 1, wherein an included angle between axes of each fibrous root and the main root is less than or equal to 45°.

13. The joint prosthesis according to claim 12, wherein the included angle between the axes of each fibrous root and the main root is 30°.

14. The joint prosthesis according to claim 1, wherein a diameter of the main root and a diameter of the fibrous roots are both 0.1-2 mm.

15. A hip joint prosthesis comprising: a hip ball prosthesis configured to be mounted on a human femur, and a hip acetabular cup prosthesis matched with the hip ball prosthesis, the hip ball prosthesis and the hip acetabular cup prosthesis being both made of the joint prosthesis of claim 1, wherein the boundary layer of the hip acetabular cup prosthesis is a curved plate structure, and the boundary layer of the hip ball prosthesis is a structure formed after a flat plate is bent multiple times, and wherein connecting lines of centers of projections of every three of the root filament clusters adjacent and closest to one another on the boundary layer form an equilateral triangle.

16. A knee joint prosthesis, characterized by a knee femoral condyle prosthesis configured to be mounted to a tibial plateau, the knee femoral condyle prosthesis being made of the joint prosthesis of claim 1, wherein the boundary layer of the knee femoral condyle prosthesis is a structure formed after a flat plate is bent multiple times, and wherein connecting lines of centers of projections of every three of the root filament clusters adjacent and closest to one another on the boundary layer form an equilateral triangle.

17. A manufacturing method of the joint prosthesis of claim 1, comprising:
- designing a three-dimensional model of the metal body;
- inputting a file of the three-dimensional model into a 3D printing device for 3D printing;
- implanting the printed metal body into a forming mold of the ceramic body, filling one side of the root layer with ceramic blank powder and a sintering aid adhesive, and closing the forming mold for pressing the ceramic blank powder and the sintering aid adhesive to form a pre-sintering blank;
- placing the pre-sintering blank after shaping into a sintering furnace for sintering to form a ceramic body bonded to the root-like filament clusters; and
- polishing a joint friction surface on the ceramic body; and
- wherein connecting lines of centers of projections of every three of the root filament clusters adjacent and closest to one another on the boundary layer form an equilateral triangle.

* * * * *